(12) United States Patent
Totman et al.

(10) Patent No.: US 7,240,564 B2
(45) Date of Patent: Jul. 10, 2007

(54) METHOD AND APPARATUS FOR DETECTING AND DETERMINING EVENT CHARACTERISTICS WITH REDUCED DATA COLLECTION

(75) Inventors: Peter D. Totman, Ogden, UT (US); Randy L. Everton, Brigham City, UT (US); Mark R. Egget, Brigham City, UT (US); David J. Macon, Ogden, UT (US)

(73) Assignee: Alliant Techsystems Inc., Edina, MN (US)

( * ) Notice: Subject to any disclaimer, the term of this patent is extended or adjusted under 35 U.S.C. 154(b) by 732 days.

(21) Appl. No.: 10/208,518

(22) Filed: Jul. 30, 2002

(65) Prior Publication Data

US 2004/0025091 A1    Feb. 5, 2004

(51) Int. Cl.
  *G01N 3/08* (2006.01)
(52) U.S. Cl. ....................................................... 73/827
(58) Field of Classification Search .................. 73/763, 73/767, 771, 774, 827
  See application file for complete search history.

(56) References Cited

U.S. PATENT DOCUMENTS

| | | | |
|---|---|---|---|
| 3,858,439 A | | 1/1975 | Nakamura |
| 4,559,946 A | | 12/1985 | Mower |
| 4,831,325 A | * | 5/1989 | Watson, Jr. .................. 324/678 |
| 5,023,901 A | * | 6/1991 | Sloan et al. ................... 379/38 |
| 5,319,291 A | | 6/1994 | Ramirez |
| 5,389,795 A | | 2/1995 | Rye |
| 5,519,643 A | * | 5/1996 | Kentrat et al. ............... 702/176 |
| 5,563,526 A | * | 10/1996 | Hastings et al. ............... 326/37 |
| 5,959,214 A | * | 9/1999 | Vaidyanthan et al. .......... 73/777 |
| 6,055,180 A | * | 4/2000 | Gudesen et al. ............ 365/175 |
| 6,243,242 B1 | | 6/2001 | Davis |
| 6,269,179 B1 | | 7/2001 | Vachtsevanos et al. |
| 6,281,564 B1 | * | 8/2001 | Richiuso ...................... 257/532 |
| 6,303,916 B1 | * | 10/2001 | Gladnick ..................... 250/205 |
| 6,386,038 B1 | * | 5/2002 | Lewis et al. ................... 73/587 |
| 6,388,404 B1 | * | 5/2002 | Schnebly et al. .............. 318/16 |
| 6,666,857 B2 | * | 12/2003 | Smith .......................... 606/12 |
| 6,741,177 B2 | * | 5/2004 | Ballantyne ............... 340/568.5 |
| 6,791,085 B2 | * | 9/2004 | Martin et al. ............ 250/338.1 |
| 6,963,036 B1 | * | 11/2005 | Zicher ......................... 177/185 |

FOREIGN PATENT DOCUMENTS

WO    WO 01/14171 A1    3/2001

\* cited by examiner

*Primary Examiner*—Max Noori
(74) *Attorney, Agent, or Firm*—TraskBritt (57) ABSTRACT

A method and apparatus for detecting and determining event characteristics such as, for example, the material failure of a component, in a manner which significantly reduces the amount of data collected. A sensor array, including a plurality of individual sensor elements, is coupled to a programmable logic device (PLD) configured to operate in a passive state and an active state. A triggering event is established such that the PLD records information only upon detection of the occurrence of the triggering event which causes a change in state within one or more of the plurality of sensor elements. Upon the occurrence of the triggering event, the change in state of the one or more sensor elements causes the PLD to record in memory which sensor element detected the event and at what time the event was detected. The PLD may be coupled with a computer for subsequent downloading and analysis of the acquired data.

48 Claims, 6 Drawing Sheets

METHOD AND APPARATUS FOR DETECTING AND DETERMINING EVENT CHARACTERISTICS WITH REDUCED DATA COLLECTION

GOVERNMENT RIGHTS

The United States Government has rights in the following invention pursuant to Contract No. NAS8-97238 between NASA and Thiokol Corporation.

BACKGROUND OF THE INVENTION

1. Field of the Invention

The present invention relates generally to the detection and determination of an event characteristic and, more particularly, to detecting and determining one or more characteristics of an event, such as, for example, the material failure of a monitored component.

2. State of the Art

It is often desirable to detect and determine various event characteristics associated with the physical response or reaction of a given component or material when subjected to various influences such as, for example, an application of a force or exposure to a specific environment for a given period of time. It is desirable to determine the response of such a component so as to accurately predict future behavior and to properly design systems and components which react and perform in a predictable manner.

For example, material testing is often performed to determine mechanical behavior of a specific material or a particular component configuration under specified conditions. Such behavior might include the determination of, for example, yield strength, fracture toughness, impact strength, fatigue limits, temperature-induced effects, corrosion or degradation rates, crack rate propagation or any of a number of other mechanical, material or physical properties.

Figure 1:
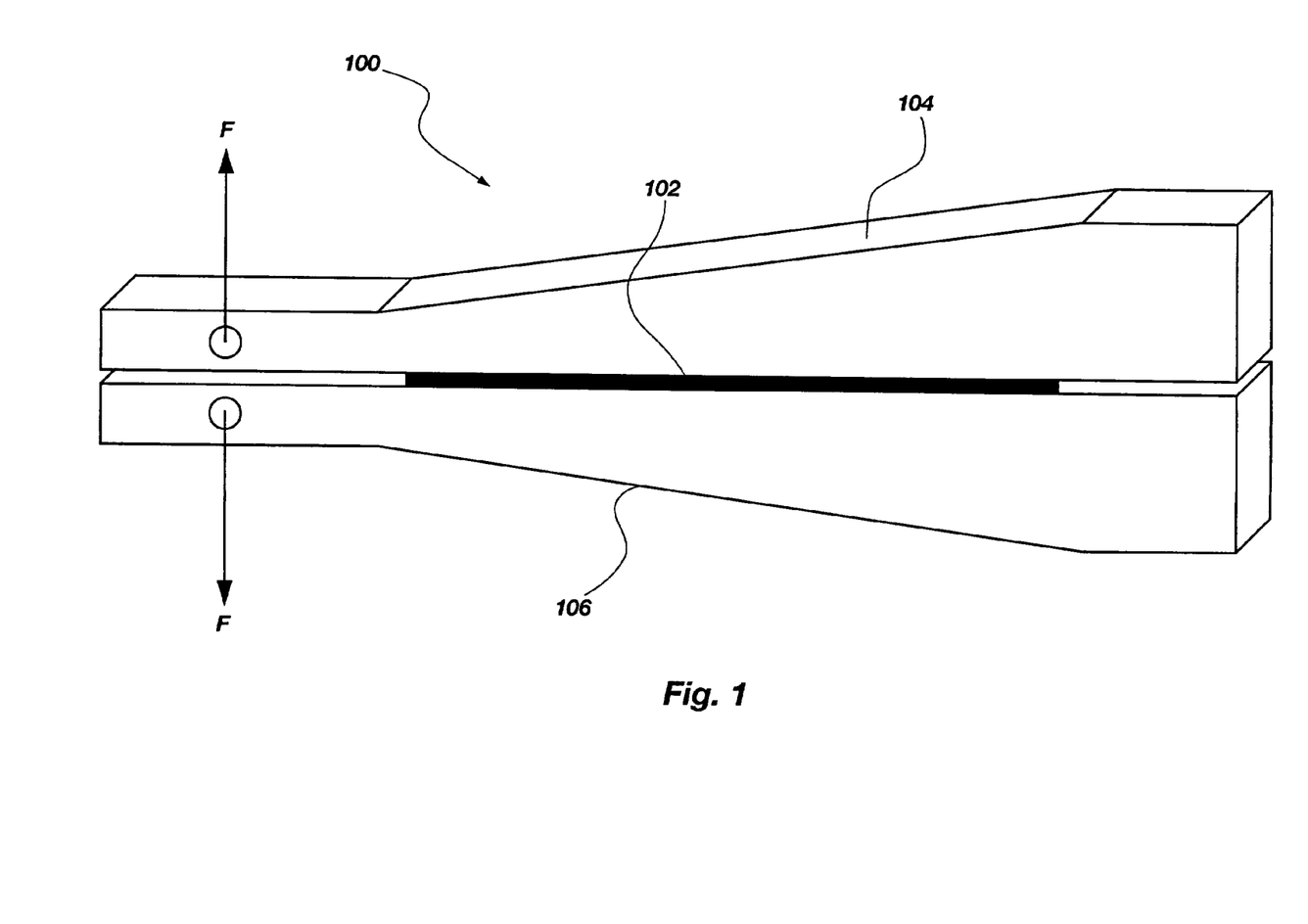
FIG. 1 is a perspective view of an exemplary conventional configuration used in one type of fracture testing.

In a more particular example, fracture tests are conventionally conducted to determine the fracture energy of an adhesive bond. One such fracture test is known as a tapered double cantilevered beam (TDCB) test. As shown in FIG. 1, a TDCB test involves a test specimen 100 having an adhesive bond 102 between two similarly configured tapered beams 104 and 106. A force "F" of known magnitude is applied to each beam 104 and 106 so as to pull the beams 104 and 106 in opposing directions. The resulting structure thus includes two beams 104 and 106 loaded in a cantilevered manner. The force F applied to the beams 104 and 106 is ultimately transferred into the adhesive bond 102, which is then monitored for material failure which manifests itself through propagation of a crack.

Conventional means of monitoring the adhesive bond 102 for failure include visual inspection and/or use of electronic equipment including, for example, one or more resistive-type propagation gages adhered to the location of interest (e.g., adjacent the adhesive bond 102) and electrically coupled to a data acquisition system. Such conventional means of monitoring the adhesive bond are labor intensive and, particularly when utilizing electronic equipment, involve considerable expense. Furthermore, such conventional means are not highly efficient. For example, if a testing specimen becomes unstable, a crack may propagate at a very high rate approaching the speed of sound for the given material being tested. In such a circumstance, it becomes impossible to obtain useful information about the crack propagation by way of visual inspection.

On the other hand, when using conventional electronic monitoring equipment, data is continuously collected over time and sample rates of up to several megahertz are required for accurate data acquisition. Thus, if a testing specimen fails over a period of time which is in excess of, for example, twenty minutes, the acquired data will include several billion data points for subsequent processing and analysis. Storing such a large amount of data wastes valuable memory or storage space since only a few of the collected data points are actually relevant and desirable for purposes of proper fracture analysis.

Additionally, as alluded to above, the cost associated with the equipment capable of sampling and recording such a large number of data points may often be prohibitive. For example, an individual resistive-type propagation gage may cost $300 (and isn't reusable) while the data acquisition equipment having an adequate sample rate may cost $8,000–$10,000 or more.

In view of the shortcomings in the art, it would be advantageous to provide an apparatus and method for determining event characteristics, such as, for example, acquiring data relative to a material or component failure, which is simple in its operation and configuration, highly efficient and relatively inexpensive.

BRIEF SUMMARY OF THE INVENTION

In accordance with one aspect of the invention, an apparatus is provided for monitoring and detecting event characteristics. The apparatus includes a sensor array including a plurality of sensor elements. A programmable logic device (PLD) is operatively coupled to the plurality of sensor elements. The PLD is configured to operate in a default passive state and an event-triggered active state. A change in state detected by any of the sensor elements may cause the PLD to switch from the passive state to the active state wherein data associated with the change in state may be stored in memory.

The apparatus may include as sensor elements, for example, break-wire sensors, piezoelectric sensors, photosensitive sensors or magnetic-type sensors. The apparatus may further include as a PLD, for example, a simple or complex PLD or a field-programmable gate array (FPGA).

In accordance with another aspect of the present invention, a system is provided for determining fracture characteristics of an adhesive material. The system includes a test specimen comprised of a first member and a second member which are coupled together with the adhesive material. A load-applying apparatus which includes at least one load-applying member is configured to apply a load to the test specimen such that the first and second members are loaded in a cantilevered manner.

A plurality of break-wire conductors are coupled to the test specimen such that they traverse the adhesive bond. The break-wire conductors may be disposed on a thin sheet of dielectric material such as, for example, a polymer to maintain a desired configuration and orientation with respect to the test specimen.

A PLD is operatively coupled to the plurality of break-wire conductors and is configured to operate in a passive state and an active state. Upon the breaking of one of any of the plurality of break-wire conductors, the PLD records information in memory regarding which of the break-wire conductors broke and at what time it broke.

In accordance with another aspect of the present invention, a method is provided for monitoring an event. The method includes establishing an event trigger such as, for example, the initiation or propagation of a crack in a material failure. A plurality of sensor elements is provided with each sensor element being configured to individually detect the event trigger. A PLD is provided and configured to operate in a passive state and an active state. Upon the detection of an event trigger in one or more of the sensor elements, the PLD switches from the passive state to the active state and data is recorded and stored corresponding with the detection of the event trigger. Such data may include which of the plurality of sensor elements detected the event trigger and at what time the event trigger was detected thereby.

BRIEF DESCRIPTION OF THE SEVERAL VIEWS OF THE DRAWINGS

The foregoing and other advantages of the invention will become apparent upon reading the following detailed description and upon reference to the drawings in which.

DETAILED DESCRIPTION OF THE INVENTION

Figure 2:
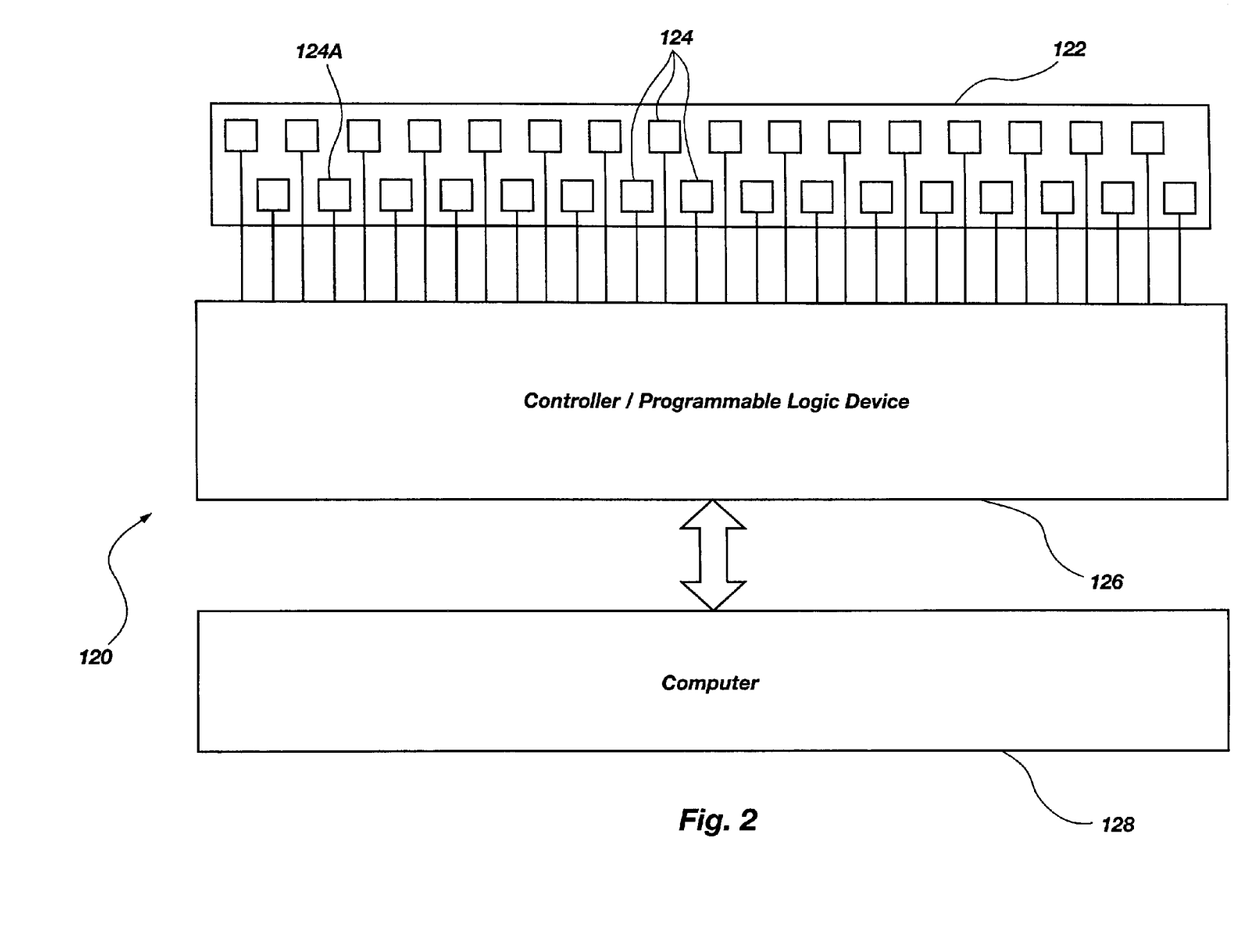
FIG. 2 shows an apparatus used in acquiring characteristic data associated with an event according to an embodiment of the present invention.

Referring to FIG. 2, an exemplary monitoring apparatus 120 is shown for detecting and/or determining one or more specified characteristics of a monitored event. The apparatus 120 includes a sensor array 122 including a plurality of individual sensor elements 124. The sensor elements 124 may include any of various types of known sensors such as, for example, electrically conductive break-type elements, pressure transducers, accelerometers, photodiodes, phototransistors, magnetic or Hall effect-type sensors, ultrasound transmitters and receivers, piezoelectric transducers and the like. Further, in some embodiments, the sensor array 122 may include multiple types of sensors arranged in combination for detection of various characteristics of the monitored event.

The sensor array 122 is operatively coupled to a programmable logic device (PLD) 126 which may include, for example, a simple programmable logic device (SPLD) (such as a programmable logic array (PLA)), a complex programmable logic device (CPLD) or a field-programmable gate array (FPGA). As shall be discussed in more detail below, the PLD 126 desirably includes a high resolution internal clock and some memory storage capacity such as, for example, random access memory (RAM).

The sensor array 122 may be coupled to and communicate with the PLD 126 by way of electrical, optical or radio frequency transmission as will be appreciated by those of ordinary skill in the art. The PLD 126 may further be operatively coupled with a computer 128 for downloading and processing of the data acquired thereby.

The PLD 126 is configured such that each individual sensor element 124 of the sensor array 122 is independently identifiable therewith and, upon the change in state in any given sensor element 124, the PLD 126 records which sensor element 124 experienced such a change in state and at what time the change in state occurred. For example, the change in state may be associated with a change in voltage such as, for example, if the sensor elements 124 include piezoelectric transducers. Thus, upon detecting such a change in state, the PLD 126 will note which of the sensor elements (e.g., 124A) experienced the change, record the time at which the change took place and store the acquired information in the memory associated with the PLD 126.

Acquiring event information in such a manner enables extraneous information (i.e., data which might be collected from the sensor elements when no change in state is occurring) to be excluded. As noted above, such extraneous information is largely irrelevant and wastes valuable memory or storage space. Thus, the acquisition of data in accordance with the present invention may be termed as being selective and "on-demand." In other words, data acquisition is an event-triggered or event-initiated process such that only discrete and discriminate data points are recorded upon occurrence of the triggering event (e.g., that which causes the change in state in a sensor element). Such is in contradistinction to the continual collection of data, regardless of its relevance, as is done in conventional prior art systems and processes.

Such a process may be efficiently accomplished by utilizing a PLD 126 operatively coupled with the individual sensor elements 124 and configured to remain in a passive or latent state until a triggering event occurs and is detected by one or more of the sensor elements 124. As will be addressed in further detail below, the use of such a device in conjunction with a clock or timing element having high resolution allows for more efficient gathering of data since no data is recorded or stored in memory unless and until the triggering event causes the change in state of one or more of the sensor elements 124.

Figure 3:
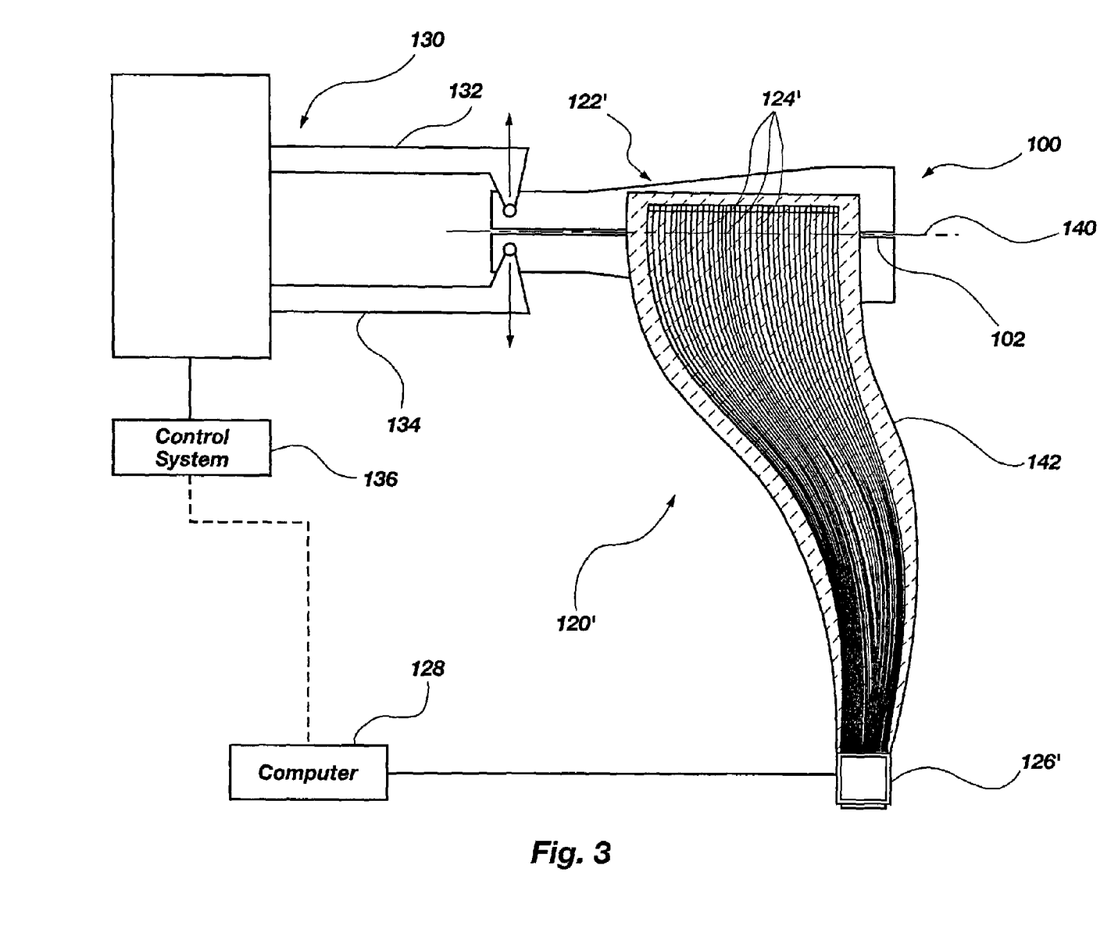
FIG. 3 shows an exemplary apparatus used in acquiring data associated with a material test according to an embodiment of the present invention.

Referring now to FIG. 3, an exemplary monitoring apparatus 120' is shown which is configured for acquiring data in conjunction with a fracture testing apparatus 130. The testing apparatus may be configured to test an exemplary specimen 100 as shown and described above with reference to FIG. 1. The fracture testing apparatus 130 may include load-applying members 132 and 134 configured to apply a predetermined load to the specimen 100. It is noted that, in another embodiment, instead of two load-applying members 132 and 134, a single load-applying member may be utilized wherein a portion of the specimen 100 is secured to a stationary fixture in substantial opposition to the load-applying member.

A control system 136 is operatively coupled with the fracture testing apparatus 130 to regulate and monitor the load applied to the specimen 100 and to record the magnitude of load as a function of time. As will be appreciated by those of skill in the art, such information will be significant in the analysis of the failure of the specimen 100.

The load-applying members 132 and 134 are coupled to the specimen 100 and configured to apply a load thereto in a substantially perpendicular manner relative to the axis or plane 140 along which failure is intended or expected. The magnitude and/or duration of the applied load may be set via the control system 136. The applied load may be constant or may vary as a function of time as is desired or necessary for a given test.

With the load being applied by the testing apparatus 130, the monitoring apparatus 120' is utilized to detect the occurrence of a crack or fracture within the specimen 100, as well as to determine the rate at which such a crack propagates once it is present.

The monitoring apparatus 120' includes a sensor array 122' having a plurality of individual sensor elements 124'. The sensor elements 124' may include, for example, electrically conductive break-type elements, also referred to as break-wires. Such break-wires 124' may be formed of, for example, small diameter copper conductors. The sensor elements 124' may be deposited on a sheet 142 of thin material such as, for example, polyimide sheeting having an exemplary thickness of approximately 1 mil (0.001 inch) and which is commercially available from DuPont under the trademarked name KAPTON®. In one exemplary embodiment, copper wires or copper traces exhibiting a thickness of approximately 3 mils (0.003 inch) may be deposited on the sheet 142 of thin material. It is noted that the break-wires 124' have been described as being deposited on the sheet 142, indicating that they may be left exposed on a surface thereof. However, if desired, the break-wires 124' may be formed within the sheet 142 or, alternatively, sandwiched between multiple sheets such that they are not exposed to the environment.

The sensor elements 124' are arranged on the sheet 142 in accordance with an expected event behavior. For example, with the expectation that a failure may occur along the axis of expected failure 140 of the specimen 100, the sensor elements 124' may be arranged in a substantially parallel manner along the sheet 142. Spacing of the sensor elements 124' may vary depending on the event being monitored, the configuration of the specimen 100 being tested and the desired resolution of data acquisition. One exemplary mutual spacing of the sensor elements 124' may include 0.050 inch.

The sensor elements 124' are operatively coupled with a PLD which, in the exemplary embodiment shown, includes an FPGA 126'. An exemplary FPGA 126' may include a SPARTAN II® Field Programmable Gate Array commercially available from Xilinx, Inc., of San Jose, Calif., although other devices are also contemplated.

It is noted that, as the sensor elements 124' extend toward the FPGA 126', the sheet 142, which likewise extends towards the FPGA 126', may increase in material thickness for protection of the sensor elements 124' in areas where event detection is not expected (e.g., locations away from the expected failure plane or axis 140). Thus, for example, the sheet 142 may increase in thickness from approximately 1 mil in the region adjacent the specimen 100 to approximately 3 mils in the region adjacent the FPGA 126'.

As with previously described embodiments, the FPGA 126' may be coupled to a computer 128 for downloading data from the FPGA 126'. The computer 128 may also be utilized in conjunction with the control system 136 so as to correlate data associated with the operation of the testing apparatus 130 (e.g., load characteristics such as magnitude, duration and variation of load over time) with the data obtained from the FPGA 126'.

For testing purposes, a portion of the sheet 142 may be coupled to the fracture specimen 100 adjacent the bond line of the adhesive bond 102 being tested. An exemplary adhesive material which may be used to adhere the sheet 142 to the specimen 100 includes a cyanoacrylate adhesive (CA) although other adhesives may be utilized. It may be desirable in certain embodiments and implementations of the present invention to use an adhesive which cures to a brittle state so as to enhance the rate at which a displacement experienced by the fracture specimen 100 is transferred, via a tear or fracture in the adhesive, to the sensor elements 124' for detection thereby.

The sensor array 122' is configured and oriented such that the sensor elements 124' are angularly positioned relative to the axis of expected failure 140, and are desirably substantially perpendicular to the axis of expected failure 140.

In operation, the testing apparatus 130 applies a force to the specimen 100 and electrical current is passed through the sensor elements 124' of the sensor array 122'. Upon experiencing sufficient loading, the specimen 100 will begin to fail, exhibiting a crack or fracture within the adhesive bond 102. The occurrence of a crack within the adhesive bond 102 will also induce a break in a sensor element 124' most adjacent to the point of failure. The break in the sensor element 124' will be detected as a change in voltage by the FPGA 126', which will then record the event by indicating which sensor element 124' experienced a change in voltage and at what time the change in voltage (or wire breaking) occurred. This information is stored in associated memory of the FPGA 126' for subsequent downloading by the computer 128 and may be used, for example, in determining the location and time of crack initiation and the rate of crack propagation.

As a crack grows or propagates, additional sensor elements 124' will break, with each in turn registering the same with the FPGA 126' to be stored in memory along with an associated time stamp. The FPGA 126' desirably includes an internal clock which has resolution of, for example, approximately $10^{-6}$ seconds so that data may be recorded at an extremely high resolution with respect to the time element.

Thus, during testing, the FPGA may be seen as bimodal, operable in both a passive state (which in the presently disclosed embodiment is the default state) and an event-triggered active state with regard to data acquisition. While the specimen 100 is under loading but not exhibiting any failure, the FPGA 126' responsively operates in a passive state in that it does not record any data or initiate any other particular functions. However, upon noting the detection of an event (e.g., a change in current or voltage) by one of the sensor elements 124', the FPGA 126' operates in the active state so as to identify which sensor element 124' has detected the event, provide a time stamp associated with such detection, and then record such information in memory. The FPGA 126' may then go back to its passive state until another event detection is made and continue in such a manner over an indefinite period of time.

It is noted that the exemplary system and apparatus shown in FIG. 3 significantly reduces the cost of data acquisition over conventional electronic means discussed above herein. For example, it is estimated that such a sensor array 124' may be obtained for approximately $20 while a suitable FPGA 126' may be obtained for approximately $150.

Figure 4:
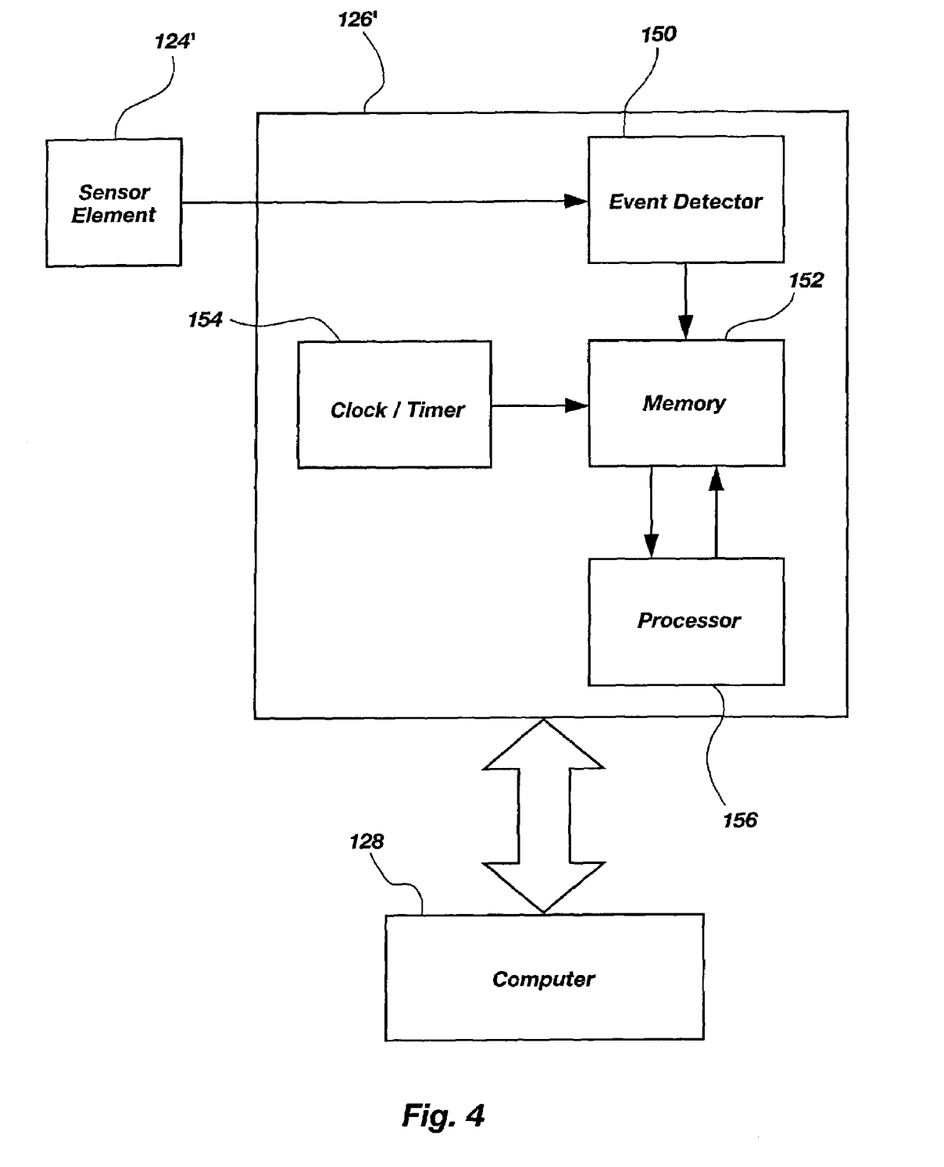
FIG. 4 is a schematic showing the input and output functions of a controller utilized in accordance with the present invention.

Referring briefly to FIG. 4, a schematic is shown of an exemplary FPGA 126'. The FPGA 126' includes an event detector 150 configured to detect the transmission of an event from a sensor element 124'. Thus, for example, a sensor element 124' may indicate that an event has occurred by way of a predetermined change in voltage or current. The event detector notes the change in voltage or current and also notes from which sensor element 124' of the sensor array 122' (FIG. 3) such information was transmitted. The event detector 150 records this information into memory 152, such as on a random access memory (RAM) chip or module, where it is stored with a time stamp indicating the time at which the detection event occurred as determined by the internal clock and timing mechanism 154.

A processor 156 is coupled with the memory 152 and configures the memory with regard to which location in memory will be associated with a given sensor element 124' and also reads such stored information so as to relay it to an external device such as the computer 128. Communication between the FPGA 126' and the computer 128 may be accomplished, for example, through a universal asynchronous receiver-transmitter (UART) and an RS-232 link as will be appreciated by those of skill in the art.

It is noted that the FPGA 126' shown is exemplary and may include additional features and components as will be recognized and appreciated by those of skill in the art. For example, various clock and software reset functions may be built into the FPGA 126'. Also, while the exemplary FPGA 126' has been shown as including an internal clock 154, other embodiments may include an external clock coupled with an internal timer/counter.

Figure 5:
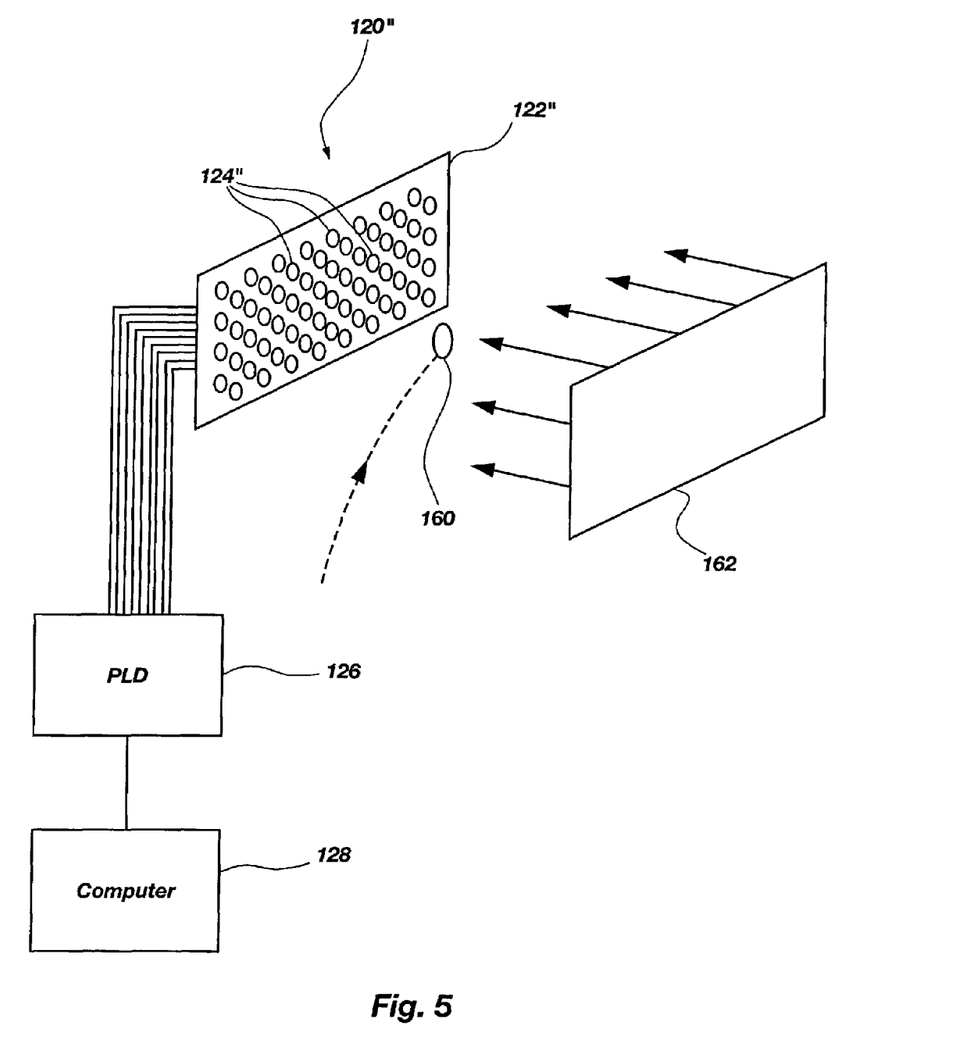
FIG. 5 shows an exemplary apparatus used in acquiring data associated with mapping the velocity and acceleration of a projectile according to an embodiment of the present invention.

Referring now to FIG. 5, a monitoring apparatus 120" is shown according to another embodiment of the present invention. The monitoring apparatus 120" is configured to monitor and detect the movement of a component 160 as it travels through a field or region. As with previous embodiments, a sensor array 122" includes a plurality of sensor elements 124". The sensor elements 124" may include, for example, photodiodes and are coupled with a PLD 126. A light source 162 is positioned a spaced distance from the sensor array 122" and provides a source of light for the sensor elements 124" to detect.

As the component 160 travels between the sensor array 122" and the light source 162, it temporarily blocks light to individual sensor elements 124". As the light is blocked from an individual sensor element 124", it indicates such to the PLD 126 by way of a signal comprising a change in current or voltage such as previously described. Again, the PLD 126 records which sensor element 124" detected the event, notes the time at which it occurred and stores such information in memory.

It is noted that in certain embodiments wherein the projectile or object being monitored emits light, the light source 162 need not be employed and the triggering event associated with collecting data may be the illumination of the photosensitive sensor elements 124" rather than the blockage of light therefrom.

In either case, as the plurality of sensor elements 124" records data, the data may be downloaded to a computer 128 and analyzed to determine such characteristics as velocity (including both speed and direction) and acceleration of the component 160.

In another embodiment, the sensor elements 124" might include magnetic or Hall-effect sensors. Thus, such sensor elements 124" may detect the induction of a magnetic field by the component 160 as it passes thereby or, alternatively, detect the change induced by the component as it travels through an already present magnetic field. The detection of such changes may again be selectively recorded by the PLD 126 and communicated to the computer 128 for appropriate processing and analysis.

In yet another embodiment, the sensor elements 124" may include ultrasound receivers and the light source 162 may be replaced with ultrasound transmitters to detect characteristics of a projectile passing therethrough and altering the ultrasound signal passing between such transmitters and receivers.

It is noted that, while described in terms of exemplary embodiments, the present invention may be applied in various fields of endeavor to monitor and detect numerous types of events. For example, such a monitoring system (120, 120', 120") may be used to detect one or more event characteristics in association with various structural failures including the rupturing of a pressure vessel (including the location, rate and direction of such a rupture), an explosion or detonation, or a vehicle crash or collision. Such a monitoring system may likewise be used to detect a shock wave in virtually any medium (gas, liquid or solid), or to measure the speed of sound in a specified material. Furthermore, the present invention may be used to monitor the rate at which a material erodes under given parameters, such as high heat and pressure conditions including, for example, the erosion of material in a rocket motor during ignition. Other examples may include the depth of penetration of a projectile into a specified material, the trajectory of shrapnel after a detonation or explosion, or the rate of such a detonation or explosion.

Another exemplary application of the present invention may be the determination of the speed of a flame front traveling down the bore of a rocket motor upon ignition thereof. Such may be detected, for example, by arranging the sensor array as a plurality of photocells which produce a voltage spike upon detecting light from the rocket's flame.

Another exemplary application of the present invention may be the monitoring of the deployment of an air bag within an automobile. For example, accelerometers or piezovelocity transducers might be coupled to a PLD and used to monitor the deployment of an air bag in order to determine the rapidity at which such an air bag deploys and/or the force generated by such a deployment.

Yet another exemplary application of the present invention may include analysis of shaped charges including the analysis of the liner upon collapse and formation of the jet produced upon detonation. For example, conventional methods of monitoring shaped charges include high-speed photography. However, the present invention enables high-speed monitoring of the detonation of a shaped charge. Furthermore, using a two-dimensional array of sensors (e.g., similar to that shown and described with respect to FIG. 5), the shape of the jet may be mapped as the jet will manifest itself by triggering sensor elements over a substantial area of an associated sensor array rather than just triggering a lineal (or curvilinear) string of sensor elements as was described with respect to monitoring a projectile.

Additionally, if multiple types of sensor elements are utilized, other characteristics may be monitored. For example, if photosensitive and magnetic sensor elements are strategically combined, one may analyze the jet produced upon detonation with the photosensitive sensor elements and also analyze the effect of detonation upon the liner with the magnetic sensors if the liner is constructed with a ferromagnetic material.

It is further noted that while the above exemplary embodiments have discussed events which occur in a relatively short period of time, the present invention may be used for detection of events which occur over significant as well as greatly extended periods of time. For example, the present invention may be used to detect and measure the growth of agricultural plants or the movement of the earth's crust along known fault lines. Of course, the present invention may be used for monitoring events which happen at intermediate rates as well.

Because data acquisition according to the present invention is an event-triggered or event-initiated process wherein only discrete and discriminate data points are recorded upon occurrence of the triggering event, the present invention may be utilized in the monitoring of events which will occur, if at all, at some indeterminate future time. For example, the present invention may be used in monitoring for an event such as an earthquake, the structural failure of a bridge or the shifting of a structure's foundation wherein the time of failure may not be for several years or decades. Thus, as described above, the present invention may operate in a passive state for a considerable period of time, requiring a minimal power draw until an event is detected, at which time it would operate in an active state to collect and store the discrete and discriminate data associated with the event.

Figure 6:
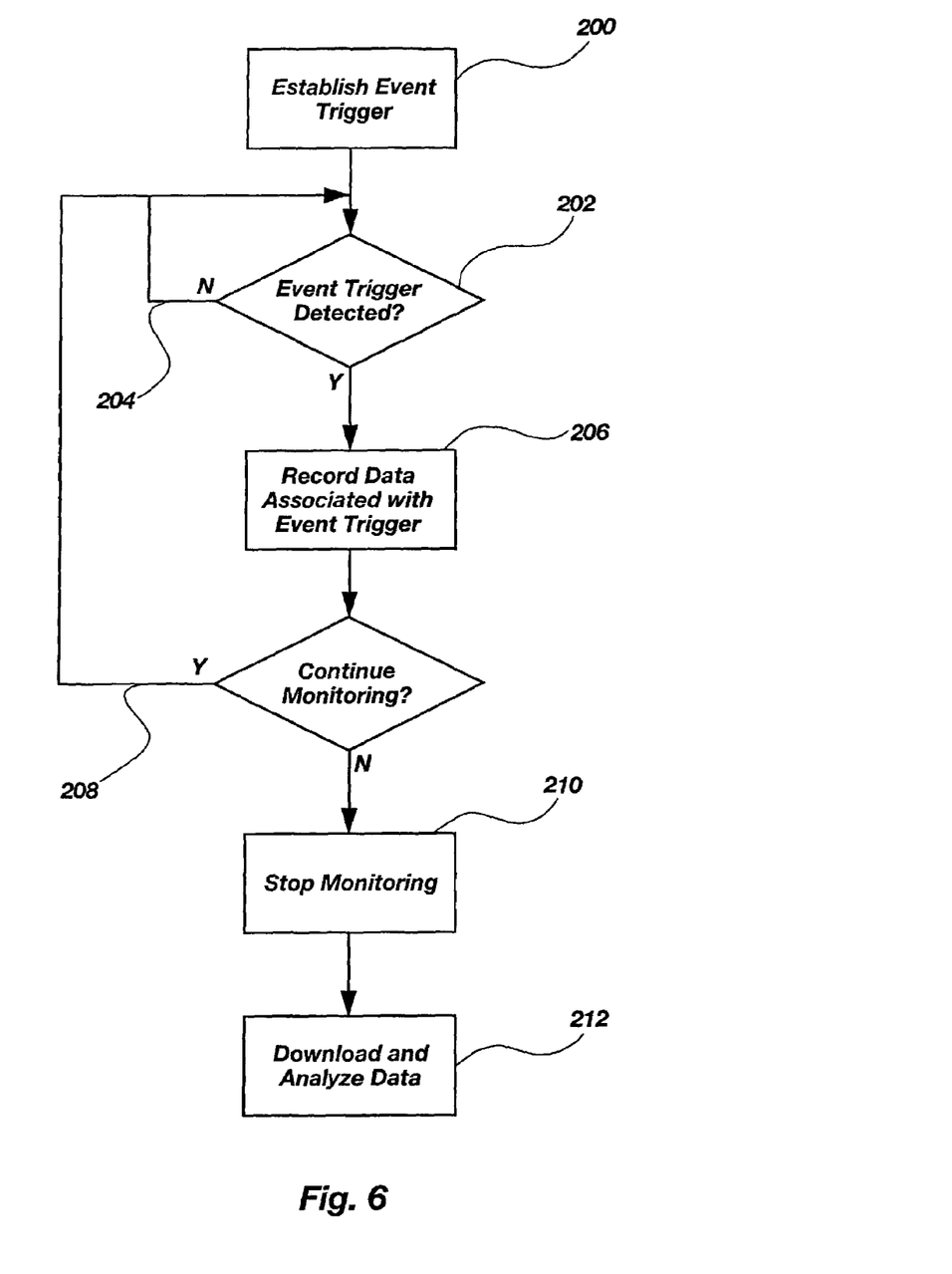
FIG. 6 is a flow chart showing the method of detecting and determining an event characteristic according to an embodiment of the present invention.

Referring now to FIG. 6, a method is shown for detecting and determining event characteristics according to an embodiment of the present invention. The method includes establishing an event trigger as indicated at 200. Establishing the event trigger may include, for example, the initiation or propagation of a crack as disclosed above. Once an event trigger is established, a monitoring apparatus, such as described above with reference to FIGS. 2–5, may be used to monitor for and detect such an event trigger as shown at 202. If an event trigger is not detected, the process continues to wait for such a detection as indicated by loop 204. If an event trigger is detected, the location of the event trigger (e.g., which sensor element of the above-described monitoring systems detected the event trigger) and the time at which the event trigger occurred is recorded in memory as shown at 206.

If monitoring is still desired, the process continues as indicated by loop 208. It is noted, however, that loop 208 should not be taken to indicate a feedback loop or to indicate the continual and sequential sampling of the sensor elements. Rather, loop 208 is simply indicative of the reiterative process of the switching between a passive state of waiting (e.g., no collection or storage of data) and an event-triggered active state of recording data associated with the event trigger.

If the monitoring process is halted, either by a system command (for example, due to the passage of a predetermined period of time without the occurrence of another event trigger) or by some type of manual override as indicated at 210, the acquired data may be extracted from memory for subsequent analysis as indicated at 212. Such analysis may include, for example, creating a time map of the detected events showing the location and timing of the detected events. Further analysis may include comparing such information with other data acquired such as, for example, from the testing apparatus 130 shown in FIG. 3.

As noted above, such a method may be utilized in various applications and may be carried out over various periods of time. For example, the method may be practiced and completed in a matter of a few seconds or minutes. On the other hand, the method may take place over a period of weeks, months or years. Similarly, the triggering event(s) may be, for example, associated with catastrophic failure or with the minute growth or movement of a given object.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes all modifications, equivalents, and alternatives falling within the spirit and scope of the invention as defined by the following appended claims.

What is claimed is:

1. An apparatus for monitoring and detecting event characteristics comprising:
   a sensor array including a plurality of sensor elements; and
   a programmable logic device (PLD) operatively coupled to the plurality of sensor elements, the PLD being configured to operate in a default passive state and an event-triggered active state, wherein the PLD is configured to record data from the sensor array only during the event-triggered active state.

2. The apparatus of claim 1, wherein a change in state occurring in any of the plurality of sensor elements causes the PLD to switch from the default passive state to the event-triggered active state.

3. The apparatus of claim 2, wherein the PLD includes a memory component having a plurality of memory locations, each of the plurality of memory locations being associated with an individual one of the plurality of sensor elements.

4. The apparatus of claim 3, wherein the PLD is configured such that a change in state of one of the plurality of sensor elements is detected by the PLD and data associated with the change in state is stored in the associated memory location of the one of the plurality of sensor elements.

5. The apparatus of claim 4, wherein the data associated with the change in state includes the time at which the change in state occurred.

6. The apparatus of claim 5, wherein the PLD is configured to be operatively coupled with a computer.

7. The apparatus of claim 2, wherein the PLD includes a field-programmable gate array (FPGA) device.

8. The apparatus of claim 7, wherein the plurality of sensor elements includes a plurality of conductors configured to break upon a detection of a predefined event to indicate the change in state.

9. The apparatus of claim 8, wherein the plurality of sensor elements are disposed on a thin sheet of dielectric material.

10. The apparatus of claim 9, wherein the thin sheet of dielectric material includes a polyimide material.

11. The apparatus of claim 9, wherein the thin sheet of dielectric material exhibits a thickness of approximately 0.001 inch at a first portion thereof which is distally located relative to the FPGA device.

12. The apparatus of claim 11, wherein the thin sheet of dielectric material tapers in thickness from the first portion to a second portion which is adjacent the FPGA device.

13. The apparatus of claim 12, wherein the thin sheet of dielectric material exhibits a thickness of approximately 0.003 inch in the second portion.

14. The apparatus of claim 9, wherein the plurality of conductors are disposed on the thin sheet of dielectric material in a substantially parallel manner.

15. The apparatus of claim 14, wherein the plurality of conductors exhibits substantially equal spacing from one another.

16. The apparatus of claim 15, wherein the plurality of conductors are spaced approximately 0.050 inch from one another.

17. The apparatus of claim 1, wherein the PLD includes a simple programmable logic device.

18. The apparatus of claim 1, wherein the PLD includes a complex programmable logic device.

19. The apparatus of claim 1, wherein the plurality of sensor elements are photosensitive.

20. The apparatus of claim 18, further comprising a light source configured and positioned to provide light to the plurality of sensor elements.

21. The apparatus of claim 1, wherein the plurality of sensor elements includes a plurality of magnetic sensors.

22. The apparatus of claim 1, wherein the plurality of sensor elements includes a plurality of piezoelectric transducers.

23. The apparatus of claim 1, wherein the PLD includes a timing device having a resolution of at least approximately $10^{-6}$ seconds.

24. A system for determining fracture characteristics of an adhesive material comprising:
a test specimen including a first member and a second member coupled together with the adhesive material;
a load-applying apparatus including at least one load-applying member configured to apply a load to the test specimen such that the first and second members are loaded in a cantilevered manner;
a plurality of break-wire conductors coupled to the test specimen; and
a programmable logic device (PLD) operatively coupled to the plurality of break-wire conductors configured to operate in a default passive state and an event-triggered active state such that upon breaking of one of any of the plurality of break-wire conductors the PLD switches from the default passive state to the event-triggered active state, wherein the PLD while in the event-triggered active state is configured to record information in memory regarding which of the break-wire conductors broke and at what time the break-wire conductor broke.

25. The system of claim 24, wherein the plurality of break-wire conductors includes copper conductors.

26. The system of claim 25, wherein the plurality of break-wire conductors are disposed on a thin dielectric sheet and wherein the thin dielectric sheet is adhered to the test specimen such that the plurality of break-wire conductors traverses a bond line formed by the adhesive material between the first member and the second member.

27. The system of claim 26, wherein the plurality of break-wire conductors are arranged to be substantially perpendicular to the bond line.

28. The system of claim 26, wherein the thin dielectric sheet includes a polyimide material.

29. The system of claim 26, wherein a portion of the thin dielectric sheet is coupled to the test specimen with an adhesive.

30. The system of claim 29, wherein the portion of the thin dielectric sheet coupled to the test specimen exhibits a material thickness of approximately 0.001 inch.

31. The system of claim 30, wherein the thin dielectric sheet exhibits a thickness of approximately 0.003 inch in a portion thereof which is located adjacent the PLD.

32. The system of claim 26, wherein the plurality of break-wire conductors are arranged in a substantially parallel manner.

33. The system of claim 32, wherein the plurality of break-wire conductors exhibits a spacing of approximately 0.050 inch from one another.

34. The system of claim 25, wherein the PLD includes a field-programmable gate array (FPGA).

35. The system of claim 25, wherein the PLD is configured to be operatively coupled to a computer.

36. The system of claim 24, wherein the PLD includes a timing mechanism which has a resolution of at least approximately $10^{-6}$ seconds.

37. A method of monitoring an event, the method comprising:
establishing an event trigger;
providing a plurality of sensor elements, each configured to individually detect the event trigger;
providing a programmable logic device (PLD) and configuring the PLD to operate in a default passive state and an event-triggered active state; and
storing data representative of one or more signals produced by any of the plurality of sensor elements only while the PLD is in the event-triggered active state, wherein storing data includes storing data regarding detection of the event trigger including which of the plurality sensor elements detected the event trigger and at what time the event trigger was detected thereby.

38. The method according to claim 37, wherein storing the time the event trigger was detected includes storing the time at a resolution of at least approximately $10^{-6}$ seconds.

39. The method according to claim 37, wherein providing a plurality of sensor elements includes providing a plurality of break-wire conductors and configuring the plurality of break-wire conductors to individually break upon the detection of the event trigger thereby.

40. The method according to claim 37, further comprising establishing the event trigger as a change in pressure.

41. The method according to claim 37, further comprising establishing the event trigger as a change in a magnetic field.

42. The method according to claim 37, further comprising establishing the event trigger as a change in a light field.

43. The method according to claim 37, further comprising downloading the stored data to a computer.

44. A method of monitoring an event, the method comprising:
establishing an event trigger;
providing a plurality of sensor elements, each configured to individually detect the event trigger;
providing a programmable logic device (PLD) and configuring the PLD to operate in a default passive state and an event-triggered active state;
upon a detection of the event trigger, storing data associated with detection of the event trigger including which of the plurality of sensor elements detected the event trigger and at what time the event trigger was detected thereby;
downloading the stored data to a computer; and
making a time map representative of the downloaded data.

45. A monitoring apparatus comprising:
a plurality of sensors configured to detect a specified event;
a programmable logic device (PLD) configured to operate in a passive state and an active state such that, when in the passive state the PLD stores no data and, when in the active state, the PLD stores in associated memory discrete and discriminate data associated with selective ones of the plurality of sensors.

46. The apparatus of claim 45, wherein the PLD switches from the passive state to the active state upon detection of the specified event by at least one of the plurality of sensors.

47. The apparatus of claim 46, wherein the PLD includes a field-programmable gate array (FPGA).

48. The apparatus of claim 45, wherein the PLD is configured to be operatively coupled with a computer.

* * * * *

UNITED STATES PATENT AND TRADEMARK OFFICE
CERTIFICATE OF CORRECTION

| | |
|---|---|
| PATENT NO. | : 7,240,564 B2 |
| APPLICATION NO. | : 10/208518 |
| DATED | : July 10, 2007 |
| INVENTOR(S) | : Peter D. Totman et al. |

It is certified that error appears in the above-identified patent and that said Letters Patent is hereby corrected as shown below:

On the title page:
In ITEM (75) Inventors: change "Mark R. Egget, Brigham City, UT (US);" to --Mark R. Eggett, Brigham City, UT (US);--

CLAIM 37, COLUMN 12, LINE 14, after "plurality" and before "sensor" insert --of--

Signed and Sealed this

Twenty-ninth Day of September, 2009

David J. Kappos
*Director of the United States Patent and Trademark Office*